United States Patent [19]
Little

[11] Patent Number: 5,826,458
[45] Date of Patent: Oct. 27, 1998

[54] MOISTURE DETECTION METER

[75] Inventor: Cosmo Little, Falmouth, United Kingdom

[73] Assignee: Scapa Group PLC, Blackburn, United Kingdom

[21] Appl. No.: 809,939

[22] PCT Filed: Oct. 5, 1995

[86] PCT No.: PCT/GB95/02366

§ 371 Date: Apr. 3, 1997

§ 102(e) Date: Apr. 3, 1997

[87] PCT Pub. No.: WO96/11410

PCT Pub. Date: Apr. 18, 1996

[30] Foreign Application Priority Data

Oct. 6, 1994 [GB] United Kingdom .................. 9420217

[51] Int. Cl.⁶ .......................... G01R 27/26; B29C 71/04; G01N 5/02; H05B 9/06

[52] U.S. Cl. .............................. 73/73; 73/29.01; 324/634; 324/636; 324/640

[58] Field of Search .................. 73/73, 29.01, 159; 324/633, 634, 636, 637, 640

[56] References Cited

U.S. PATENT DOCUMENTS

| | | | |
|---|---|---|---|
| 3,586,971 | 6/1971 | Bosisio | 324/58.5 C |
| 3,597,566 | 8/1971 | Johnson | 219/10.55 |
| 3,883,798 | 5/1975 | Free | 324/58.5 C |
| 4,042,879 | 8/1977 | Ho et al. | 324/58.5 C |
| 4,381,485 | 4/1983 | Steinbrecher | 324/58 C |
| 4,829,233 | 5/1989 | Flemming et al. | 324/58.5 C |
| 4,904,928 | 2/1990 | Lewis | 324/636 |
| 5,046,356 | 9/1991 | Osaki et al. | 73/73 |
| 5,333,493 | 8/1994 | Cutmore | 73/73 |
| 5,334,941 | 8/1994 | King | 324/637 |
| 5,554,935 | 9/1996 | Kraszewski et al. | 324/637 |
| 5,621,330 | 4/1997 | Greenwald et al. | 324/640 |
| 5,648,038 | 7/1997 | Faithi et al. | 264/406 |
| 5,666,061 | 9/1997 | Assenheim | 324/636 |
| 5,686,841 | 11/1997 | Stolarczyk et al. | 324/635 |

*Primary Examiner*—Hezron E. Williams
*Assistant Examiner*—J. David Wiggins
*Attorney, Agent, or Firm*—Jacobson, Price, Holman & Stern, PLLC

[57] ABSTRACT

A moisture detection meter (10) has a sensing head having a single chamber (11) with an open top. A dielectric resonator member (14) is provided in the chamber. The sensing head also has a field generator (17) to generate an oscillating electric fluid in the chamber. The resonator member (14) and the field interact to produce at least one field component which is directed out of the open top of the chamber to interact with stock passing over the sensing head. A detection device is also provided to detect the frequency of resonance of the field compact after interaction with the stock and an indicator device is provided so as to give an output indicative of the moisture content of the stock.

12 Claims, 3 Drawing Sheets

5,826,458

MOISTURE DETECTION METER

BACKGROUND OF THE INVENTION

This invention relates to a moisture detection meter particularly but not exclusively suited for use in the forming section, or 'wet end' of a Fourdrinier or other papermaking machine.

At the wet end of a Fourdrinier machine a water/fibre stock is applied to the surface of a moving drainage fabric at an upstream end of a forming section of the machine. Water is removed and a drained fibre layer is delivered for further processing and drying at a downstream end of the section.

It is desirable to be able to monitor the drainage efficiency along the forming section and therefore it is known to use microwave detection meters in a sensing head placed beneath the drainage fabric which detect the quantity of moisture by measuring the frequency of resonance of microwaves which are directed into the fabric and stock. In such an arrangement, it is usual to have more than one microwave cavity in order that a fixed frequency reference can be compared to a sensed frequency of resonance and the difference therebetween can be determined. The determined difference is indicative of the moisture content of the stock.

A problem arises due to the necessity to use more than one cavity in the sensing head insofar as a minimum limit is placed on the dimensions of the head which can restrict the position in the machine at which the sensor can be placed.

SUMMARY OF THE INVENTION

It is an object of the present invention to provide a moisture detection meter in which the dimensions of the sensing head can be substantially reduced thereby increasing the possibilities for location of the meter in the machine.

According to the present invention therefore there is provided a moisture detection meter comprising a sensing head having a single chamber which is open upwardly, a dielectric resonator member in said chamber and field generation means to generate an oscillating electric field in said chamber, said resonator member and said field interacting to produce at least one field component which is directed out of said open top of said chamber to interact with stock passing over the sensing head, detection means to detect the frequency of resonance of said field component after interaction with said stock and an indicator device operable to provide an output indicative of the moisture content of said stock.

With this arrangement it is possible to provide a moisture meter which has a sensing head of substantially reduced dimensions.

Preferably said dielectric resonator has a relatively high dielectric constant at the frequency of operation and may be substantially equal to 80.

Preferably said open top of said chamber is covered with at least one layer of a material having a low permittivity thereby permitting the field component to exit the chamber and interact with the stock without significant perturbation or attenuation. The material may conveniently be polytetrafluoroethylene (PTFE) which is a low loss, low permittivity material.

Preferably the frequency of the oscillating field generated by the field generating means is substantially 1 GHz and most preferably in the range 0.6 to 0.75 GHz.

Preferably the field generating means is connected to a voltage controlled oscillator which is tunable so as to be capable of providing an oscillating signal to the field generating means over a predetermined frequency range. Preferably the field generating means comprises an electrical coupling mounted adjacent to said resonator member along a transverse axis thereof. With such an arrangement, perturbation of the electric field provided by the generating means by the dielectric resonator material, produces one field component of sufficient strength to exit the chamber through the open top, whilst minimising the strength of other field components.

Preferably the detection means includes peak detection means and/or means for tracking a peak across a frequency range to detect a peak signal which occurs at resonance. Preferably both peak detection means and means for tracking a peak are used and the latter may be embodied conveniently in the form of a suitably programmed computer. Thus the means for tracking a peak may comprise a suitably programmed microprocessor or computer.

The invention will now be described further by way of example only and with reference to the accompanying drawings of which:

DETAILED DESCRIPTION OF THE PREFERRED EMBODIMENTS

Figure 1:
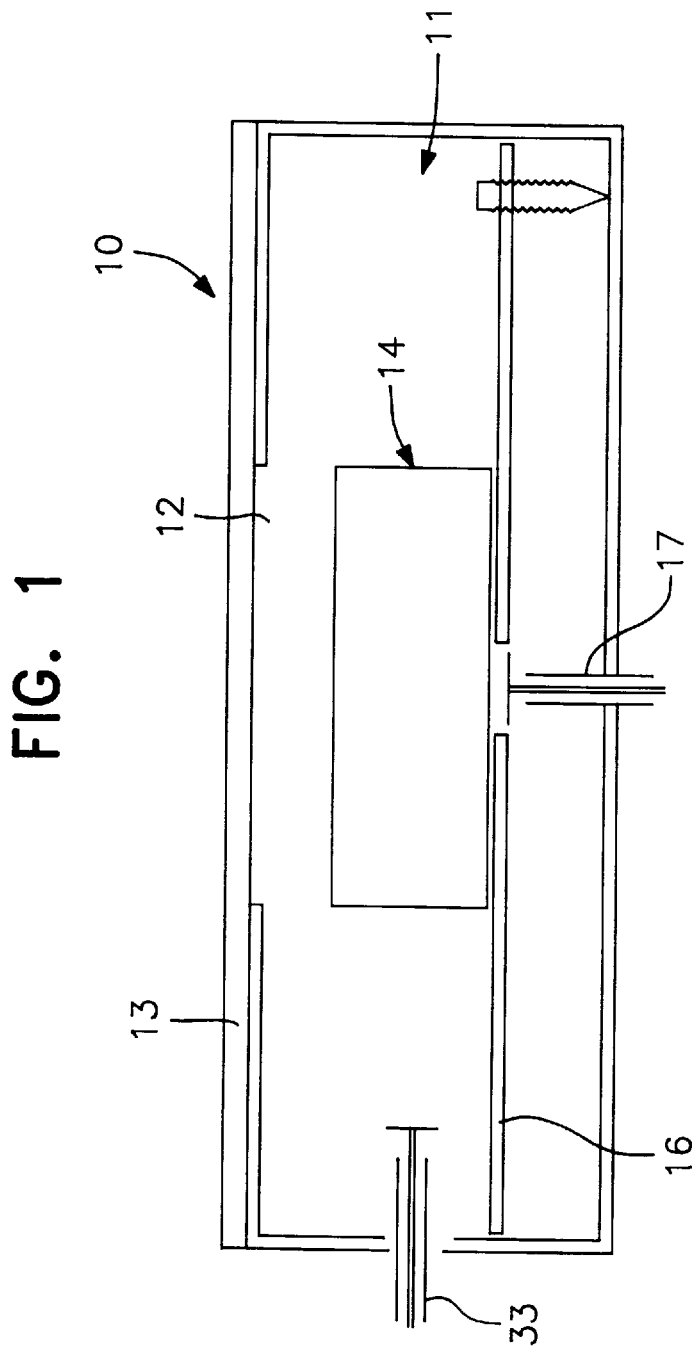
FIG. 1 shows a diagrammatic representation of one form of moisture drainage meter according to the present invention.

Referring now to the drawings, there is shown in FIG. 1 a diagrammatic layout of one form of sensing head 10 in accordance with the present invention. The sensing head 10 comprises an enclosed cavity 11 having an aperture 12 in a top thereof. The aperture 12 is closed off by a layer 13 of low permittivity low loss (at high frequency) material, e.g. polytetrafluoroethylene (PTFE). A block of dielectric material 14 is mounted in the cavity 11 in any suitable manner as desired or as appropriate. The block may be supported on a height adjustable floor surface 16 within the cavity 11 as shown in the figure.

An electrical coupling 17 projects through a base of the cavity and terminates in an electrical plate, or loosely wound turns of conductor, adjacent to, but spaced from, a lower surface of the dielectric block 14.

Figure 2:
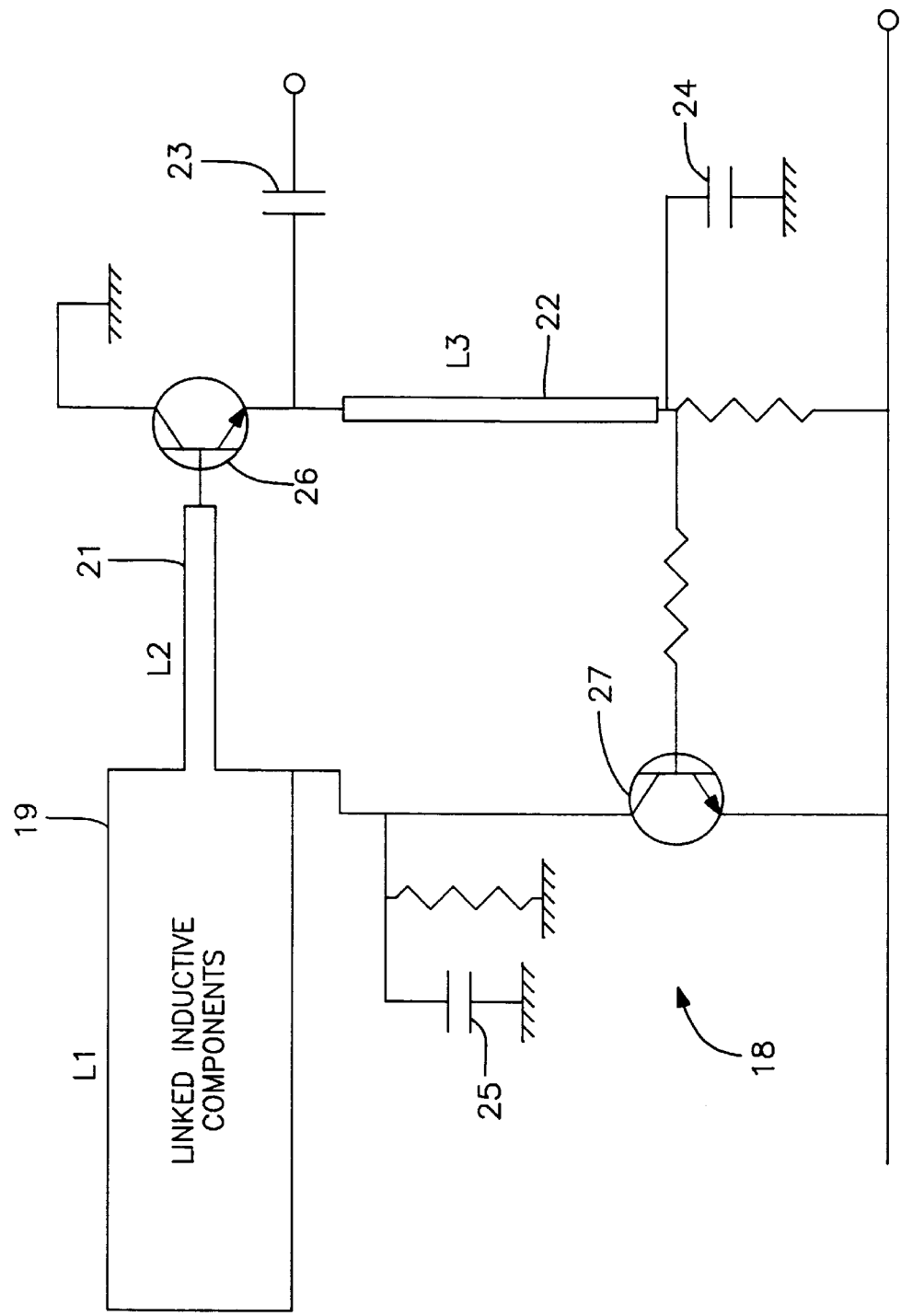
FIG. 2 shows a circuit diagram of a part of one form of control circuitry for the meter of FIG. 1.

The electrical coupling 17 is linked to a voltage controlled oscillator 20 circuit 18 of conventional form, shown in FIG. 2, which comprises linked inductive 19, 21, 22 and capacitive components 23, 24, 25 to form an LC resonant circuit. The circuit used is active circuit in conventional manner through the use of bipolar transistors 26, 27 to provide an amplifier-like effect which results in high gain at the resonant frequency of the circuit. Whilst, given that high frequencies are being used (of the order of 1 GHz), it is preferred to use an inductive and capacitive oscillator circuit in order to reduce distortion, it might be possible to use a resistive capacitance (RC) oscillator circuit in applications where the distortion of the oscillating signal provided is less significant.

The electrical coupling 17 comprises a link coupling in which the signal from the VCO circuit is coupled to the coupling via closely spaced coils (not shown). The ratio of turns of wire in the closely spaced coils is such that the signal is stepped down voltage wise by the coupling 17.

The VCO circuit is linked to a frequency counter circuit 28 which can receive the frequency at which the VCO is resonant in conventional manner using a frequency divider 29 to drive a counter 31 under the control of a microprocessor 32.

Figure 3:
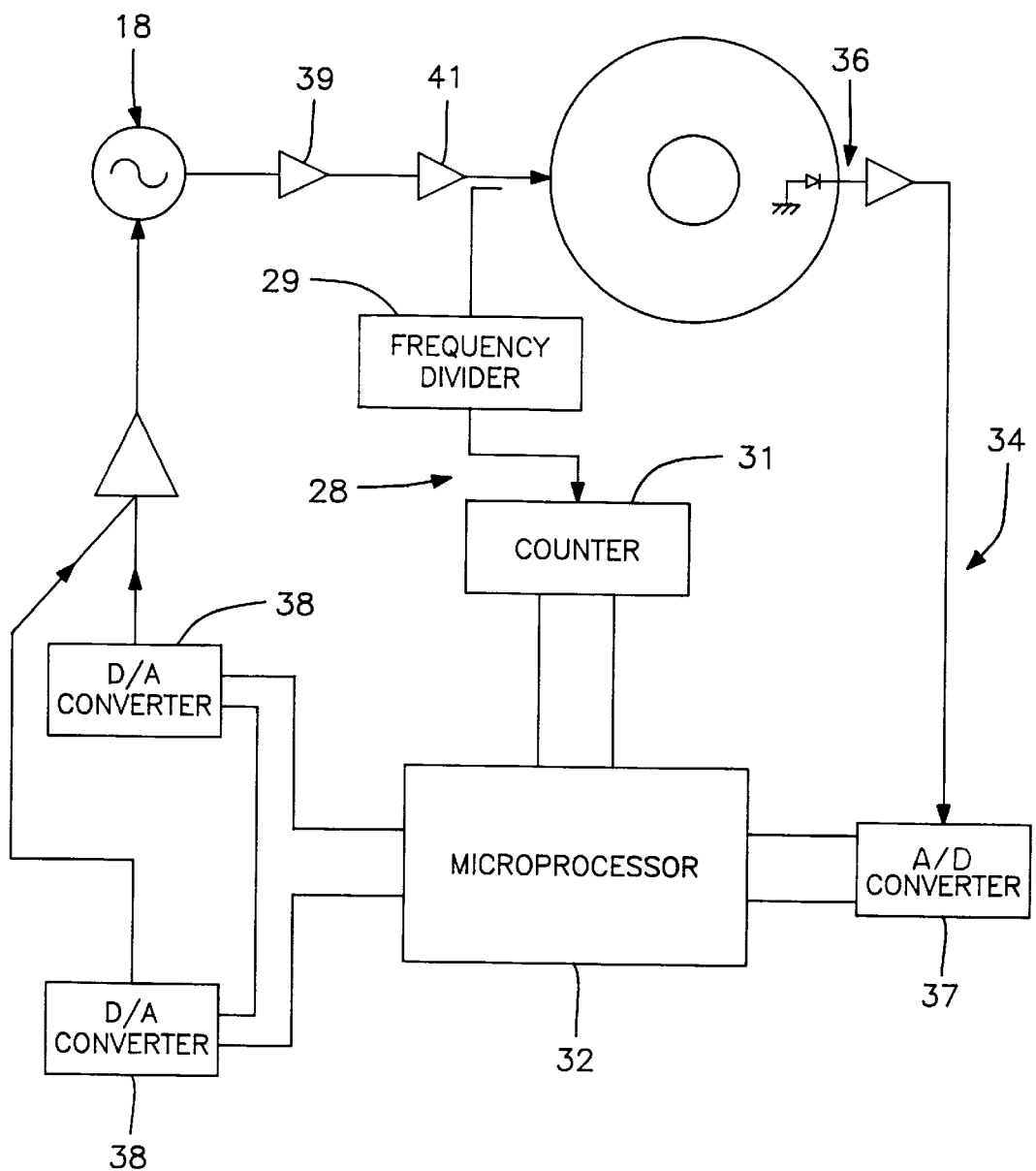
FIG. 3 shows a circuit diagram of one form of control circuitry for the meter of FIG. 1.

A second electrical coupling 33 projects inwardly from a side wall of the cavity 11 along an axis generally at right angles to the angle of the first electrical coupling 17. This second electrical coupling 33 is connected to a frequency feedback circuit 34 (see FIG. 3). This frequency feedback circuit 34 acts to receive the frequency of the oscillating signal in the cavity produced by the VCO circuit 18 and, via microprocessor 32, tunes the VCO 18 to ensure that the oscillating signal is supplied at the required frequency.

Thus the oscillating signal is rectified using a simple diode rectifier arrangement 36, then converted into a digital signal by an analogue to digital converter 37 and this digital signal is fed to the microprocessor 32. The microprocessor 32 compares the signal frequency with a predetermined value and then tunes the frequency of signal produced by the VCO circuit 18 via a output from a digital to analogue converter 38. Thus the microprocessor 32 can be the central processing unit of a computer (not shown) and in this case desired information such as required frequency either can be input via a keyboard or other input data or equipment controlling device and can be displayed on a visual display unit (VDU) associated with the computer.

In use, the VCO circuit 18 is driven to produce an oscillating signal at a desired frequency (in the present invention, the preferred frequency is in the range 0.6 to 0.75 GHz). This signal is supplied to the first electrical coupling 17 via buffer amplifiers 39, 41, the coupling 17 acting to step down the signal and supply the stepped down signal to the dielectric block 14 in the cavity 11. The oscillating signal produces an oscillating field in the block 14 which is perturbed by the dielectric block 14. The perturbed field produced by the block 14 has a number of components which are substantially confined within the extent of the block 14 due to the change in dielectric constant at the boundary of the block (at high frequencies the dielectric constant of the block 14 being approximately 80 and that of air at the same frequency being approximately $5.37 \times 10^{-6}$). However, one component of the perturbed field is able to escape the confines of the extent of the dielectric block 14 and this oscillating signal escapes through the aperture 12 in the cavity 11 and interacts with the stock passing over the PTFE layer 13. As the permittivity of the PTFE layer 13 is low, this layer has negligible effect on the signal.

The oscillating signal is modified by the stock due to the change in dielectric constant (the dielectric constant of water at high frequency being 80) and the frequency of the oscillating signal is changed. The extent of modification to the oscillation frequency is dependent upon the quantity of water in the stock. Thus the modified signal causes resonance in the dielectric block 14. The frequency feedback circuit 34, in the manner mentioned above, tunes the voltage control oscillator 18, via the microprocessor 32, to ensure that the VCO circuit 18 generates the required frequency of oscillating signal. Thus it is possible under the control of the microprocessor 32 for the signal provided by the VCO circuit 18 to be varied to ensure that accurate recognition of any changes in the resonance frequencies can be identified. For example, the microprocessor 32 may be programmed such that the resonant frequency can be tracked if the same varies.

The frequency control circuit. 28 detects the frequency of resonance in the dielectric block 14 and feeds this information to the microprocessor 32, this information being directly indicative of the quantity of water in the stock.

Thus, once the meter 10 has been calibrated, and this information is stored in the microprocessor 32, any measured resonant frequency can be identified with a particular quantity of water in the stock and this value can be output in any convenient manner using a display or printer or any other display device as desired or as appropriate.

The present invention leads to-considerable advantages insofar as since only one cavity is used, the size and bulk of sensing head can be reduced significantly, thus easing problems of location of the head under the drainage fabric.

I claim:

1. A moisture detection meter for measuring moisture content of a water/fiber mixture in a stock disposed above said meter comprising a sensing head having a single chamber which is open in an upwardly direction at an open top thereof, a dielectric resonator member in said chamber and field generation means having an electrical coupling mounted adjacent to the resonator member to generate an oscillating electric field in said chamber, whereby said resonator member and said field can interact to produce at least one field component which is directed out of said open top of said chamber to interact with the stock passing over the sensing head, detection means to detect the frequency of resonance of said field component after interaction with said stock and an indicator device operable to provide an output indicative of a moisture content of said stock.

2. A moisture detection meter as claimed in claim 1, wherein the dielectric resonator has a dielectric constant at the frequency of operation substantially equal to 80.

3. A moisture detection meter as claimed in claim 1, wherein the open top of said chamber is covered with at least one layer of a material having a low permittivity.

4. A moisture detection meter as claimed in claim 3, wherein the said material comprises polytetrafluoroethylene.

5. A moisture detection meter as claimed in claim 1, wherein the frequency of the oscillating field generated by the field generation means is in the range from 0.6 to 0.75 GHz.

6. A moisture detection meter as claimed in claim 1, wherein the field generation means is connected to a voltage controlled oscillator which is tunable so as to be capable of providing an oscillating signal to the field generation means over a predetermined frequency range.

7. A moisture detection meter as claimed in claim 1, wherein the electrical coupling is mounted along a transverse axis of said resonator member.

8. A moisture detection meter as claimed in claim 1, wherein the detection means includes peak detection means and/or means for tracking a peak across a frequency range to detect a peak signal which occurs at resonance.

9. A moisture detection, meter as claimed in claim 8, wherein the detection means further includes means for tracking a peak across a frequency range to detect a peak signal which occurs at resonance.

10. A moisture detection meter as claimed in claim 9, wherein the means for tracking a peak comprises a suitably programmed microprocessor or computer.

11. A moisture detection meter as claimed in claim 1, wherein the detection means includes means for tracking a peak across a frequency range to detect a peak signal which occurs at resonance.

12. A moisture detection meter as claimed in claim 11, wherein the means for tracking a peak comprises a suitably programmed microprocessor or computer.

* * * * *